(12) United States Patent
Moak et al.

(10) Patent No.: US 11,986,254 B2
(45) Date of Patent: May 21, 2024

(54) FLUOROLESS VASCULAR SHEATH MANIPULATION AND ELECTROGRAM MONITORING

(71) Applicant: CHILDREN'S NATIONAL MEDICAL CENTER, Washington, DC (US)

(72) Inventors: Jeffrey P. Moak, Bethesda, MD (US); Henry Blicharz, Colombia, MD (US)

(73) Assignee: Children's National Medical Center, Washington, DC (US)

( * ) Notice: Subject to any disclaimer, the term of this patent is extended or adjusted under 35 U.S.C. 154(b) by 519 days.

(21) Appl. No.: 16/490,942

(22) PCT Filed: Mar. 7, 2018

(86) PCT No.: PCT/US2018/021316
§ 371 (c)(1),
(2) Date: Sep. 4, 2019

(87) PCT Pub. No.: WO2018/165277
PCT Pub. Date: Sep. 13, 2018

(65) Prior Publication Data
US 2020/0008883 A1    Jan. 9, 2020

Related U.S. Application Data

(60) Provisional application No. 62/468,577, filed on Mar. 8, 2017.

(51) Int. Cl.
*A61B 34/20* (2016.01)
*A61B 5/287* (2021.01)
(Continued)

(52) U.S. Cl.
CPC .............. *A61B 34/20* (2016.02); *A61B 5/287* (2021.01); *A61B 18/1492* (2013.01);
(Continued)

(58) Field of Classification Search
CPC ..... A61B 34/20; A61B 18/1492; A61B 5/287; A61B 2018/00351; A61B 2018/00577;
(Continued)

(56) References Cited

U.S. PATENT DOCUMENTS

| 5,281,218 A | 1/1994 | Imran |
| 5,391,199 A | 2/1995 | Ben-Haim |

(Continued)

FOREIGN PATENT DOCUMENTS

WO    2016205328 A1    12/2016

OTHER PUBLICATIONS

Clark, Bradley C., et al. "Getting to zero: impact of electroanatomical mapping on fluoroscopy use in pediatric catheter ablation." Journal of Interventional Cardiac Electrophysiology 46.2 (2016): 183-189.

(Continued)

*Primary Examiner* — Joseph A Stoklosa
*Assistant Examiner* — Annie L Shoulders
(74) *Attorney, Agent, or Firm* — Meunier Carlin & Curfman LLC

(57) ABSTRACT

The disclosed apparatus comprises an intravascular sheath and dilator that can be placed over a guidewire after percutaneous vascular access. One or more electrodes are positioned axially at or near the distal end of the dilator, facilitating guidance of the sheath to the heart without fluoroscopy (i.e., by using electrical and/or magnetic guidance). The electrodes are in electrical conductance with leads via wires that extending proximally from the electrodes on or through the wall of the dilator or sheath.

18 Claims, 4 Drawing Sheets

(51) Int. Cl.
  A61B 17/34    (2006.01)
  A61B 18/14    (2006.01)
  A61M 25/00    (2006.01)
  A61M 29/00    (2006.01)
  A61B 18/00    (2006.01)
  A61M 25/01    (2006.01)

(52) U.S. Cl.
  CPC ......... *A61M 29/00* (2013.01); *A61B 17/3478* (2013.01); *A61B 2018/00351* (2013.01); *A61B 2018/00577* (2013.01); *A61B 2018/00839* (2013.01); *A61B 2018/1425* (2013.01); *A61B 2018/1475* (2013.01); *A61B 2034/2051* (2016.02); *A61B 2562/0209* (2013.01); *A61M 25/0082* (2013.01); *A61M 2025/0166* (2013.01)

(58) Field of Classification Search
  CPC .. A61B 2018/00839; A61B 2018/1425; A61B 2018/1475; A61M 29/00
  See application file for complete search history.

(56) References Cited

U.S. PATENT DOCUMENTS

| | | | | |
|---|---|---|---|---|
| 7,270,662 | B2* | 9/2007 | Visram | A61B 18/1492 606/41 |
| 2004/0082850 | A1* | 4/2004 | Bonner | A61B 5/06 600/424 |
| 2004/0133113 | A1* | 7/2004 | Krishnan | A61M 25/0662 600/508 |
| 2006/0089637 | A1* | 4/2006 | Werneth | A61B 18/18 606/41 |
| 2007/0106233 | A1* | 5/2007 | Huang | A61M 25/0119 606/108 |
| 2010/0317961 | A1* | 12/2010 | Jenkins | A61B 5/287 600/411 |
| 2011/0224666 | A1 | 9/2011 | Davies et al. | |
| 2012/0010490 | A1* | 1/2012 | Kauphusman | A61B 5/287 600/373 |
| 2012/0065597 | A1 | 3/2012 | Cohen | |
| 2014/0266207 | A1* | 9/2014 | Karmarkar | A61B 18/1492 324/322 |
| 2014/0275980 | A1* | 9/2014 | Flores | A61B 18/1492 600/421 |
| 2017/0014159 | A1* | 1/2017 | Stokes | A61B 5/7405 |
| 2022/0095979 | A1* | 3/2022 | Shimada | A61N 1/056 |

OTHER PUBLICATIONS

Von Alvensleben, Johannes C., et al. "Transseptal access in pediatric and congenital electrophysiology procedures: defining risk." Journal of Interventional Cardiac Electrophysiology 41.3 (2014): 273-277.

Limacher MC, et al. "ACC expert consensus document. Radiation safety in the practice of cardiology. American College of Cardiology." J Am Coll Cardiol 1998 31:892-913.

Ablation Catheters Overview 5F Rf Marinr | Medtronic accessed Mar. 2017. Available on-line at: http://www.medtronic.com/usen/healthcareprofessionals/products/cardiacrhythm/ablationarrhythmias/5frfmarinrscseries.html 3 pages.

Mark J Earley, How to perform a transseptal puncture. Heart 2009; 95:85-92. doi:10.1136/hrt.2007.135939.

Baylis Medical. NRG® Transseptal Needle. Available on-line at: https://www.baylismedical.com/system/resource_files/PRM-00034%20EN%20NRG%20Brochure%20Digital%20Spreads%20J-1,2,3%20V-2.pdf 2015-2017, 3 pages.

St. Jude Medical. BRK Transseptal Puncture Needles, 2012, 2 pages. Available on-line at: https://pdf.medicalexpo.com/pdf/st-jude-medical/atrial-fibrillation-product-catalog/70886-91093.html#open.

Swartz™ Braided Transseptal Guiding Introducers SL Series, Daig transseptal sheath, 4 pages, 2013. Available on-line at: http://www.cardion.cz/file/832/swartz-introducers-specsheets.pdf.

International Preliminary Report on Patentability issued for Application No. PCT/US2018/021316, dated Sep. 19, 2019.

International Search Report and Written Opinion in PCT/US2018/021316. Mailed May 17, 2018. 8 pages.

* cited by examiner

FLUOROLESS VASCULAR SHEATH MANIPULATION AND ELECTROGRAM MONITORING

RELATED APPLICATIONS

This application is a national stage application filed under 35 U.S.C. § 371 of PCT/US2018/021316 filed Mar. 7, 2018, which claims the benefit of U.S. Provisional Application No. 62/468,577, filed Mar. 8, 2017, which is hereby incorporated herein by reference in its entirety.

BACKGROUND

Cardiac ablation has become the method of choice for treating cardiac arrhythmias. However, concern exists around exposing the pediatric population to radiation during such treatments. With the advent and increased use of 3D electroanatomic (EA) mapping in the study and ablation of supraventricular arrhythmias, the use of radiation-intensive fluoroscopic guidance has decreased. However, given limited alternative techniques, it is still challenging to access the left heart without employing x-ray exposure. Arrhythmias originating in the left atrium are particularly challenging to ablate due to the need to route a sheath and catheter through the interatrial septum, a technique known as transseptal puncture (TS).

Prior work has demonstrated that the majority of residual fluoroscopy exposure in ablation procedures is related to transseptal (TS) puncture (Clark B C, et al. J Interv Card Electrophysiol 2016 46(2):183-189). In the past, TS puncture was performed primarily under fluoroscopic guidance. Over time, additional imaging techniques, including transesophgeal echocardiography (TEE) and intracardiac echocardiography (ICE) have been used in concert with fluoroscopy in order to decrease radiation exposure and minimize risk of the procedure. While the reported incidence of complications related to TS puncture has been as low as 0.3% (von Alvensleben J C, et al. J Interv Card Electrophysiol 2014 41:273-277), there is still a substantial risk of significant morbidity and mortality. While fluoroscopy guides the operator to a smaller target area for performing the transseptal puncture, uncertainty about true orientation of the needle position exists. The risks of TS puncture include injury to venous structures, atrial perforation, aortic perforation and pericardial effusion.

Despite the use of supplementary imaging techniques for TS puncture, the fluoroscopy that is still required remains a radiation exposure risk. While the absolute risk is unknown, the potential risks have been well documented. Radiation has the potential of both deterministic, including erythema, desquamation, cataracts, decreased white blood cell count, organ atrophy, fibrosis and sterility, and stochastic effects, including increased cancer risk and genetic abnormalities (Limacher M C, et al. J Am Coll Cardiol 1998 31:892-913). The prospect of multiple repeat procedures and catheterizations, specifically in the congenital heart disease patients, creates further impetus to reduce radiation exposure.

SUMMARY

Fluoroscopy-free TS puncture may represent the final step towards the elimination of fluoroscopy in supraventricular arrhythmia ablation procedures. Disclosed herein are devices and methods for undertaking fluoroscopy-free cardiac procedures, such as TS puncture. The disclosed apparatus comprises an intravascular sheath and dilator that can be placed over a guidewire after percutaneous vascular access. One or more electrodes are positioned axially at or near the distal end of the dilator, facilitating guidance of the sheath to the heart without fluoroscopy (i.e., by using electrical and/or magnetic guidance). The electrodes are in electrical conductance with leads via wires that extend proximally from the electrodes on or through the wall of the dilator and sheath. In some embodiments the apparatus can be used in conjunction with a system that includes a guidewire.

The apparatus disclosed herein includes a sheath comprising a proximal end, a distal end, an outer surface having a diameter sized for introduction into a blood vessel of a subject, and a lumen extending between the proximal and distal ends of the sheath. A dilator is positioned within the sheath lumen and extends distally past the distal end of the sheath. The dilator includes a proximal end, a distal end, and a lumen extending between the proximal and distal ends of the dilator. An electrode is positioned at or near the distal end of the dilator. The apparatus further includes a transseptal needle that is retractably positioned within the dilator lumen. The transseptal needle includes a proximal end and a distal end.

In some embodiments, the first electrode is circumferentially disposed at or near the distal end of the dilator. For example, the first electrode can be positioned proximally from 1 to 10 mm from the distal end of the dilator. The first electrode is suitable for electromagnetic positioning and electrogram recording. It can include a conductive material such as, for example, mylar ribbon or a metal such as platinum-iridium. A lead can connect to the first electrode. Some embodiments include a second electrode positioned at or near the distal end of the sheath. In some embodiments, the second electrode can be spaced from the first electrode by a distance of from 1 to 5 millimeters, and can also be connected to a lead. Certain embodiments of the second electrode are suitable for electromagnetic positioning, electrogram recording, and radiofrequency puncturing. Some embodiments can include a third electrode positioned proximal to the first electrode, and some embodiments can further include a fourth electrode positioned proximal to the first electrode. The fourth electrode can be spaced from the third electrode by a distance of from 1 to 5 millimeters.

In some embodiments, a transseptal needle electrode formed of a material such as, for example, stainless steel, is positioned at or near the distal end of the transseptal needle. A lead in electrical conductance with the transseptal needle electrode can also be included. In some embodiments, the transseptal needle is configured to induce focal ablation of an atrial septum, for example, by radiofrequency ablation.

The sheath of the apparatus can formed from a plastic selected from polypropylene, PTFE, polyethylene, or any combination thereof. In some embodiments, the sheath can also include a hydrophilic coating. The diameter of the outer surface of the sheath can be, for example, from 6 to 11 French. The dilator of the apparatus can also be formed from a plastic selected from polypropylene, PTFE, polyethylene, or any combination thereof, and include a hydrophilic coating.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
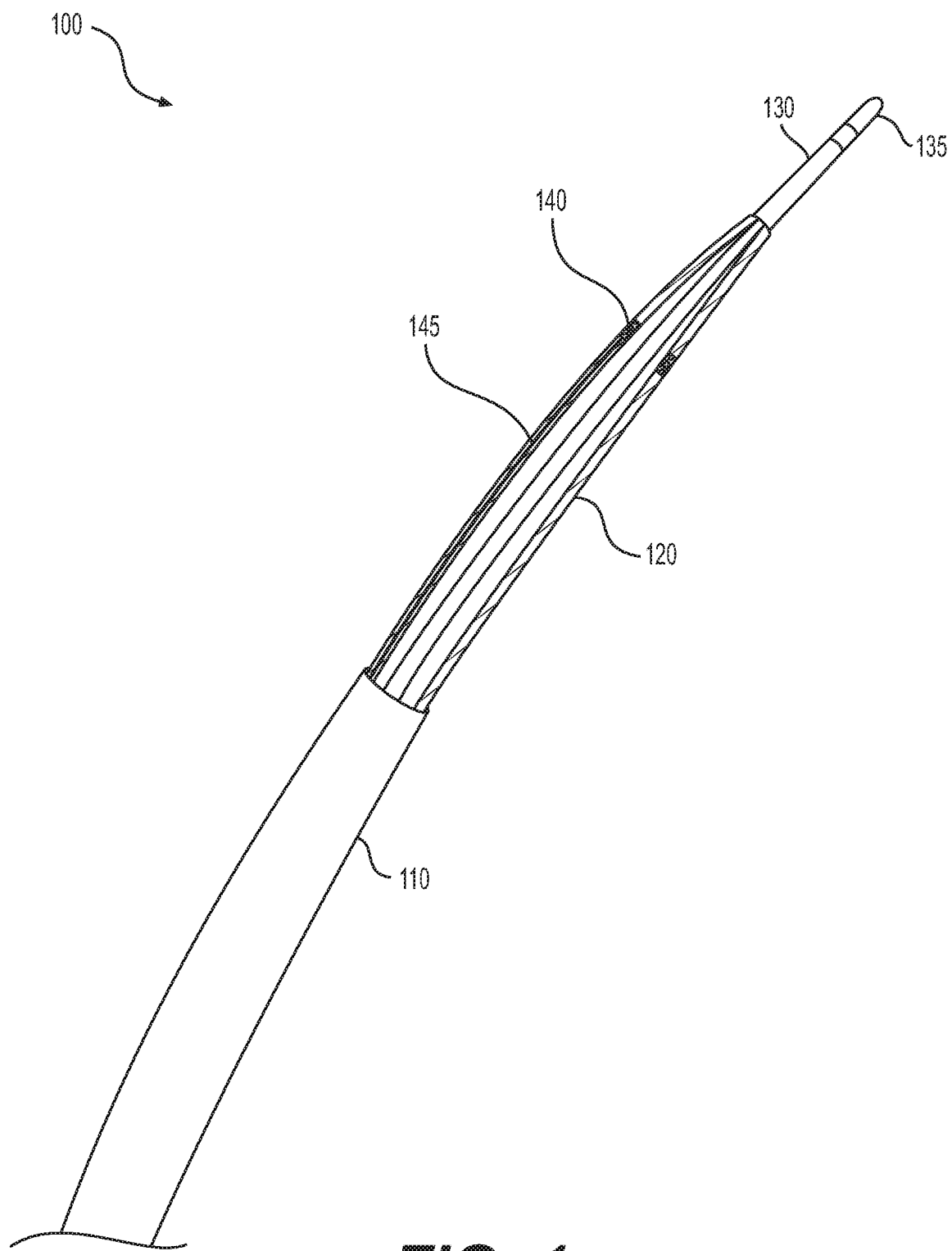
FIG. 1 is a cut out view of a distal region of an embodiment of the disclosed apparatus.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

The words "proximal", "proximally", "distal", and "distally" are orientation terms. "Proximal" and "proximally", as used herein, indicates a position closer to the person performing the procedure (and farther from the procedure site). "Distal" and "distally", as used herein, indicate positions farther from the person performing the procedure (and closer to the procedure site).

Fluoroscopy-free TS puncture may represent the final step towards the elimination of fluoroscopy in supraventricular arrhythmia ablation procedures. As noted above, arrhythmias that originate in the left atrium are especially difficult to access without potentially detrimental fluoroscopic techniques. While electromagnetic mapping is promising for certain procedures, it typically requires a separate electrophysiology catheter. Furthermore, the accuracy and resolution are too low to safely and predictably perform pediatric transseptal puncture using conventional catheters, particularly without the use of fluoroscopy.

The device disclosed herein offers at least three advantages over conventional approaches. One advantage is an increased resolution that enables the cardiac ablationist to access the left atrium without fluoroscopy. A second advantage is the ability of the device to ablate the interatrial septum, which reduces risks of cardiac perforation by obviating the need to physically push a needle. A third advantage is the ability to record intracardiac electrograms from the transseptal apparatus, decreasing the need to employ additional mapping catheters.

Turning to FIG. 1, the disclosed apparatus 100 comprises an intravascular sheath 110 having a proximal end, a distal end, and an outer surface with a diameter sized for introduction into a blood vessel. In some embodiments, the diameter of the outer surface of the sheath can be from 6 to 11 French. A lumen extends between the proximal and distal ends of the sheath 110. Sheath 110 can be formed from a variety of materials, including, but not limited to, polypropylene, polytetrafluoroethylene, polyethylene, or any combination thereof. The sheath 110 can also include a hydrophilic coating to reduce friction and clotting risks as it travels the vascular system.

Apparatus 100 also includes a dilator 120 that can be placed over a guidewire after percutaneous vascular access. The dilator includes an outer surface, a proximal end, a distal end terminating in a tapered distal tip, and a lumen extending between the proximal and distal ends of the dilator. The dilator 120 is positioned within the lumen of sheath 110, and can retract proximally into the sheath lumen or extend past the distal end of the sheath 110, as shown in FIG. 1. Dilator 120 can be formed from a variety of materials, including, but not limited to, polypropylene, polytetrafluoroethylene, polyethylene, or any combination thereof. The dilator 120 can also include a hydrophilic coating to reduce friction and clotting risks. The dilator is stiffer than the sheath, allowing enhanced manipulation capability. The dilator 120 also facilitates the transition of the sheath through a small hole, such as the one made in the interatrial septum for accessing the left atrium. The dilator 120 gently and gradually enlarges the small hole created by the needle to allow passage of the sheath 110.

The distal end of the sheath 110 can be constructed to create a smooth transition from the sheath 110 to the dilator 120. For example, the sidewall of the sheath 110 can become increasingly thinner moving distally along the sheath to avoid creating an abrupt transition between the sheath 110 and dilator 120. This smooth transition can facilitate the movement of the sheath 110 into the left atrium. In some embodiments, the distance between the distal end of the dilator 120 and the distal end of the sheath 110 can be, for example, from 1 to 3 millimeters. The distance between the outer surface of the dilator 120 and the inner surface of the sheath 110 can also vary based on the needs of the particular application.

One or more electrodes 140 can be positioned axially at or near the distal end of the dilator 120. These electrode(s) 140 can connected by a wire 145 extending proximally on or through the dilator 120 outer surface to a lead 147 that is in electrical conductance with the electrode 140 (leads 147a/147b/147c shown in FIG. 3). The electrode(s) is suitable for electromagnetic positioning, for example, using Carto® (Biosense Webster, Diamond Bar, California, U.S.A.), EnSite™ (St. Jude Medical Endocardial Solutions, Inc., St. Paul, MN, U.S.A.), or another electromagnetic imaging system, as outlined in the methods below. This facilitates the manipulation of apparatus 100 without fluoroscopy. The electrode(s) are suitable for electrogram recording. The electrode(s) comprise a conductive material. For example, in some embodiments, the conductive material could include a mylar ribbon or a metal such as platinum-iridium. The electrode 140 can be positioned anywhere from about 1 millimeter to about 10 millimeters from the distal end of the dilator 120, including about 1 millimeter, about 2 millimeters, about 3 millimeters, about 4 millimeters, about 5 millimeters, about 6 millimeters, about 7 millimeters, about 8 millimeters, about 9 millimeters, and about 10 millimeters from the distal end of the dilator 120.

Figure 3:
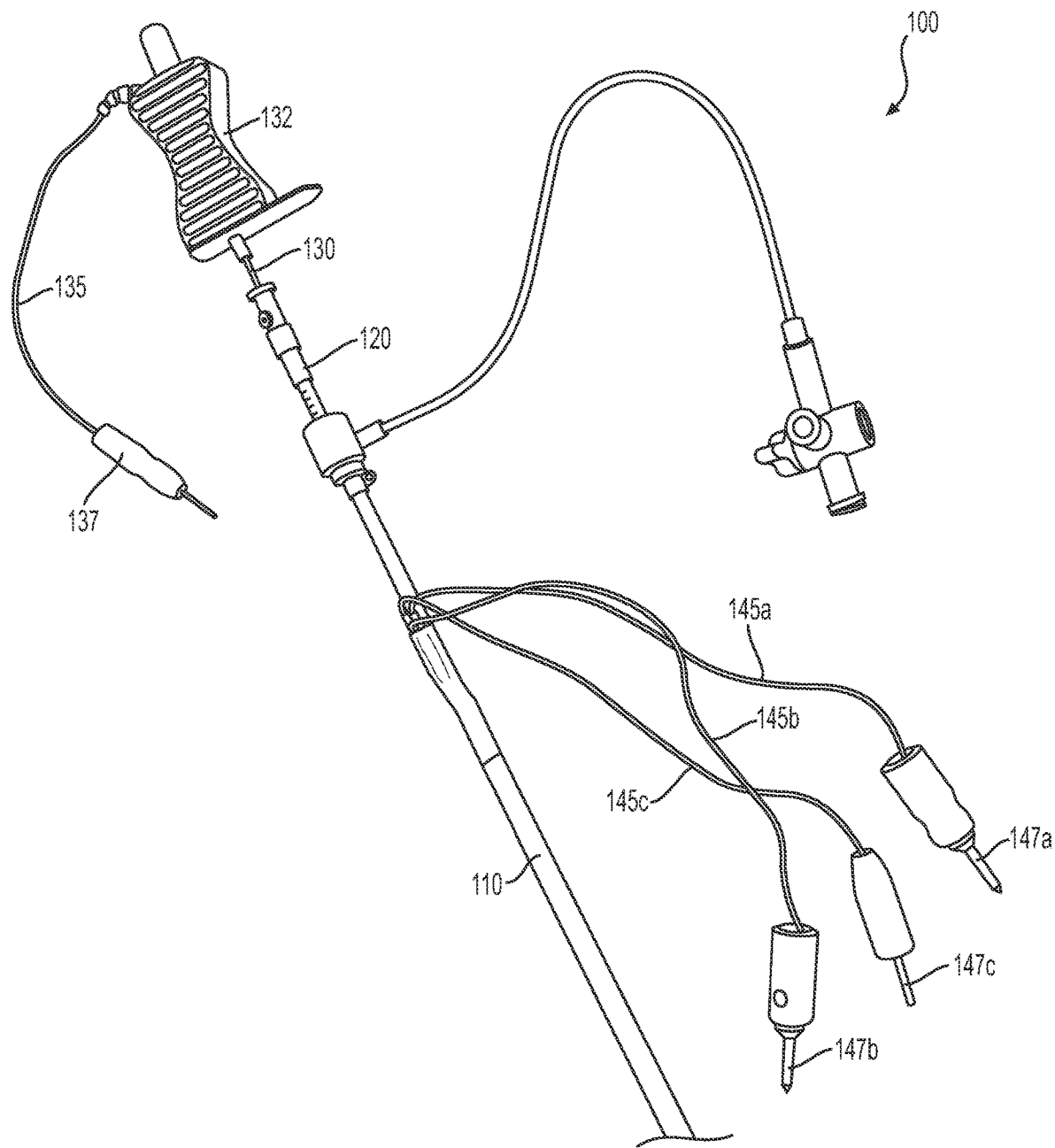
FIG. 3 is a perspective view of a proximal region of an embodiment of the disclosed apparatus.

A retractable transseptal needle 130 can be placed through the lumen of the dilator 120. The transseptal needle 130 is flexible and extends the length of sheath. As shown in FIG. 3, a lead 137 can also be connected to the proximal end 132 of the transseptal needle 130. A wire can extend through the side wall of the transseptal needle, allowing electrical continuity between the lead 137 at the proximal end 132 and the electrode at the distal end 135 of the transseptal needle 130. This enables the distal end 135 to function as an electrode for electrogram recording, as explained below.

Figure 4:
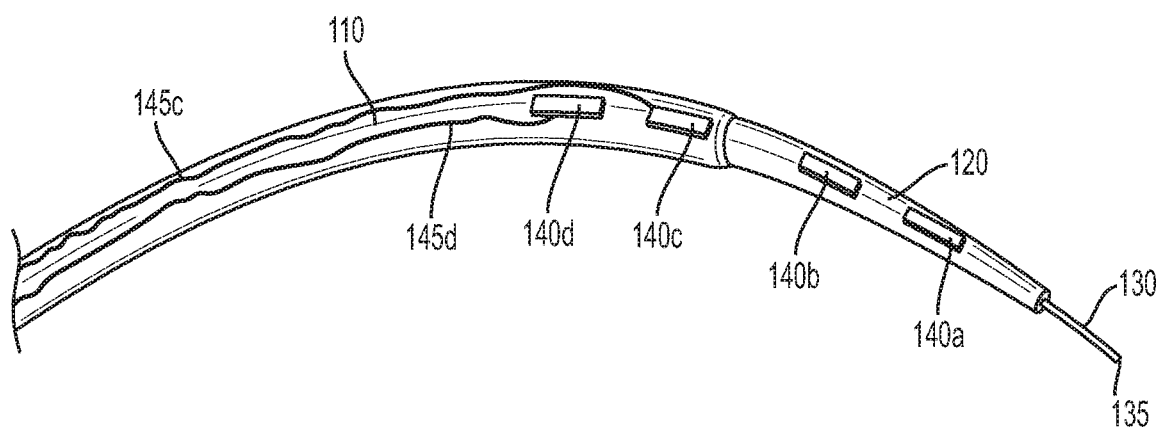
FIG. 4 is a perspective view of the distal region of an embodiment of the disclosed apparatus.

Furthermore, a magnetic-field sensor can be included at distal end 135 of the transseptal needle that enables electromagnetic positioning and monitoring of sheath location within a cardiac chamber, such as by using a Carto® electromagnetic guidance system (Biosense Webster, Diamond Bar, California, U.S.A.). Using such a guidance system, the magnetic-field sensor detects the strength of magnetic fields generated by magnetic coils placed below or near the patient, and the generated data is used to triangulate the position of the distal end 135 of the needle 130. Particularly, the Carto® mapping system (Biosense Webster, Diamond Bar, California, U.S.A.) uses a magnetic field with a strength of from $5\times10^{-6}$ to $5\times10^{-5}$ Tesla. The magnetic field is delivered from three coils placed below or near the patient, and is detected by the magnetic-field sensor at the distal end 135 of the apparatus 100. The strength measured by the magnetic-field sensor diminishes as the distance increases between a coil and the distal end 135. The magnetic forces measured by the magnetic-field sensor can be converted into the distances between each of the three coils and the magnetic-field sensor, enabling triangulation of its position in space. Apparatus 100 is equipped with at least one electrode pair (e.g. the electrode at distal end 135 paired with the electrode 140 as shown in FIG. 1), and sometimes multiple electrode pairs. For example, in FIG. 2, electrode 135 can be paired with electrode 140a, 140b, or 140c. Electrode 140a can be paired with electrode 135, 140b, or 140c. Electrode 140b can be paired with electrode 135, 140a, or 140c. Electrode 140c can be paired with electrode 135, 140a, or 140b. In FIG. 4, electrode 135 can be paired with electrode 140a, 140b, 140c, or 140d. Electrode 140a can be paired with electrode 135, 140b, 140c, or 140d. Electrode 140b can be paired with electrode 135, 140a, 140c, or 140d. Electrode 140c can be paired with electrode 135, 140a, 140b, or 140d. Electrode 140d can be paired with electrode 135, 140a, 140b, or 140c. These electrode pairs can also facilitate magnetic positioning and/or recording of local endocardial activation times. For example, the embodiment shown in FIG. 4 has distal and proximal electrode pairs 140a/140b and 140c/140d for measuring electrophysiological activity while simultaneously recording its position in space to generate a three dimensional map of the cardiac chambers.

The distal end 135 of transseptal needle 130 can also be used for focal ablation of the atrial septum, for example, ultrasound, optical, radiofrequency ablation. This radiofrequency ablation capability enables advancement of the sheath 110 across the atrial septum and into the left atrium. Because there is no need to physically push the needle, the disclosed apparatus reduces risks of atrial perforation, aortic perforation, pericardial effusion, or other injury to cardiac structures. Transseptal needle 130 can be formed of a metal material, such as, for example, stainless steel. In some embodiments, the needle can be a Radiofrequency NRG® Transseptal Needle (Baylis Medical, Boston, Massachusetts, U.S.A.) or a BRK™ transseptal needle (St. Jude, St. Paul, MN, U.S.A.). The transseptal needle 130 can, in some embodiments, incorporate a curve. The curve can be optimized, for example, for reaching the foramen ovale in a pediatric sized heart. Some embodiments of the transseptal needle 130 can incorporate an inner lumen. The inner lumen of the transseptal needle 130 can be useful, for example, in taking pressure measurements or for delivering a fluid. Some embodiments of the transseptal needle 130 can include an electrical insulation material. For example, some can be electrically insulated in all areas except for the distal tip 135. This could be useful, for example, when an electrode at the distal tip 135 is paired with other electrodes along the dilator and/or sheath, as described above.

Figure 2:
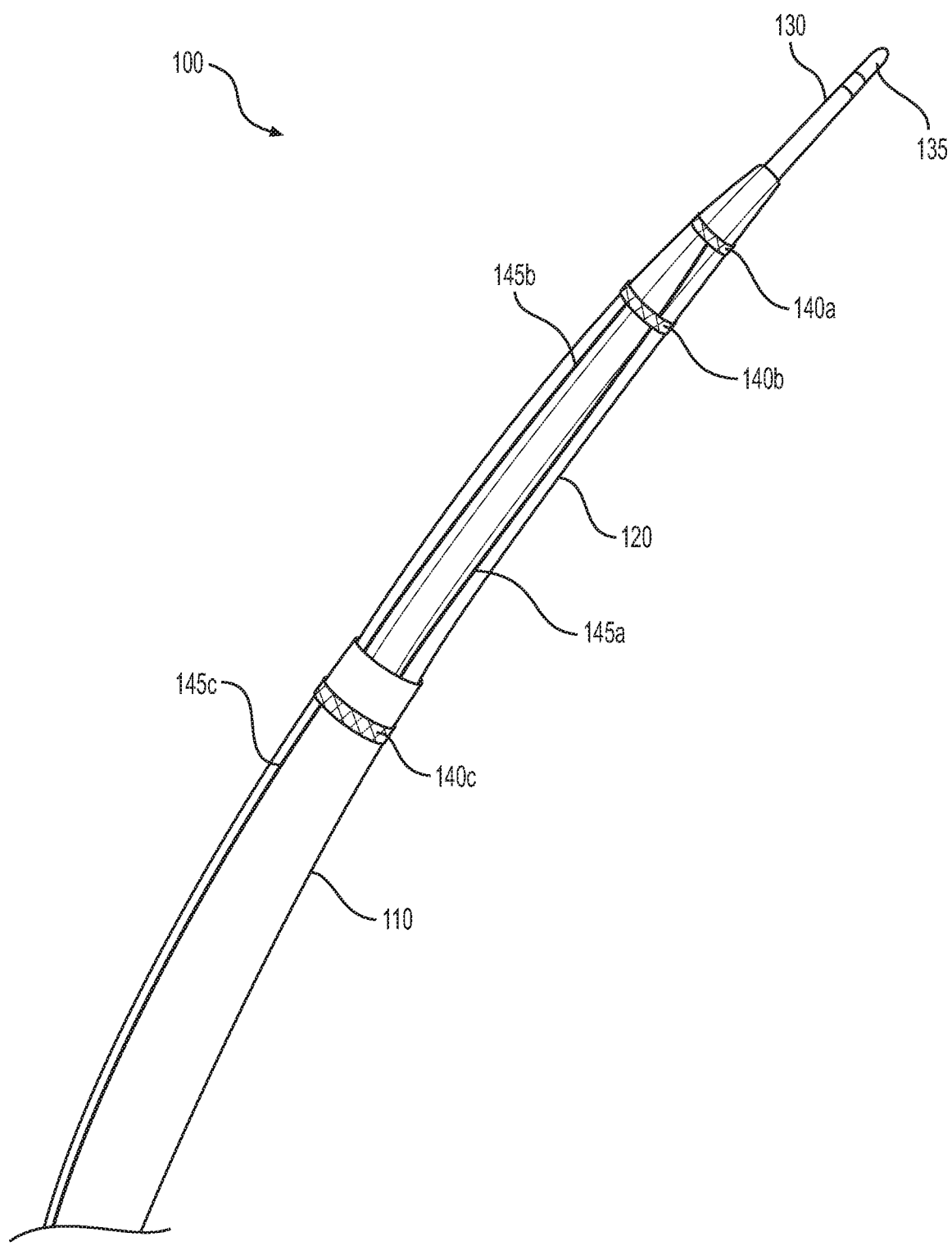
FIG. 2 is a perspective view of a distal region of an embodiment of the disclosed apparatus.

FIG. 2 depicts a device with two electrodes 140a/140b positioned axially near the distal end of the dilator 120, and one electrode 140c positioned axially near the distal end of the sheath 110. Each electrode 140a/140b/140c is connected by a separate wire 145a/145b/145c to a separate lead 147a/147b/147c (leads shown in FIG. 3). The wires can extend along the outer surface of the sheath, or through the sidewall of the sheath. FIG. 1, for example, shows wire 145 extending through the side wall of dilator 120. FIG. 2, for example, shows wires 145a, 145b, and 145c extending proximally on the outer surface of dilator 120. The wires allow each electrode to be used in both electrogram recording and magnetic positioning.

The embodiment shown in FIG. 4 has an additional electrode, 140d, located proximal to electrode 140c near the distal end of the sheath 110. The addition of electrode 140d can further improve resolution and facilitate the localization of the sheath 110 within the cardiac chambers. This will allow for using transseptal needles that do not emit radiofrequency energy. In the embodiment shown in FIG. 4 (and for all of the previously described embodiments), each of the electrodes 140a/140b/140c/140d and distal end electrode 135 is capable generating unipolar recordings and/or participating in bipolar recordings with any of the other electrodes on the apparatus 100. Furthermore, the contribution of an individual electrode or an electrode pair can change over time. For example, after the transseptal needle 130 moves through the interatrial septum, it may be retracted into dilator 120. The software controlling the system can then stop recording from the retracted transseptal needle electrode while continuing to record from electrodes 140a/140b/140c and 140d. Thus, the disclosed apparatus 100 can generate a wide variety of data for constructing electrograms of the tissue of interest.

The distance between two bipolar recording electrodes contributes to the precision with which a source of a particular electrical signal can be located and ablated (for example, when ablating an arrhythmogenic region of cardiac tissue). Narrower distances are preferred, because a signal of interest located between a pair of electrodes could potentially be underneath either the distal or the proximal electrode (but the ablating energy will only be emitted from the proximal electrode). Generally, spacing between two adjacent electrodes will be from about 1 millimeter to about 5 millimeters, including about 1 millimeter, about 2 millimeters, about 3 millimeters, about 4 millimeters, and about 5 millimeters. Incorporating multiple pairs of bipolar recording electrodes enables a practitioner to probe the direction of wavefront travel and better locate a potentially arrhythmogenic area of tissue. Furthermore, as noted above, electrode pairs can assist in electromagnetic positioning.

FIG. 4 demonstrates some potential dimensions for the electrodes and the spacing between the electrodes. In contrast to the electrodes shown in FIG. 2, which are circumferentially disposed around the sheath 110 or dilator 120, the electrodes shown in FIG. 4 extend in axially longitudinally along the sheath or dilator. In cross section, the electrodes could be circular (extend circumferentially fully around the sheath as shown in FIG. 2), or they could extend circumferentially only partly around the sheath, creating a semicircle or some other arc of a circle, as shown in FIG. 4. In the embodiment of FIG. 4, each electrode 140a, 140b, 140c, and 140d measures 2 millimeters axially along the sheath 110 or the dilator 120. The distal-most electrode 140a is positioned 2 millimeters from the distal end of dilator 120. Electrode 140b is positioned 2 millimeters proximally from the proximal end of electrode 140a. A 4 millimeter space exists between electrodes 140b and 140c. In some embodiments, 3 millimeters of this space are located on dilator 120, and 1 millimeter of the 4 millimeter space is located at the distal end of the sheath 110. Finally, electrode 140d is positioned 2 millimeters proximally from the proximal end of electrode 140c. However, these distances are only one example and are not meant to be limiting of the scope of the disclosure. For example, two adjacent electrodes could be spaced by anywhere from 1 to 5 millimeters and still participate in bipolar recordings of electrophysiological signals.

The apparatus 100 can be used in a variety of fluoroscopy-free cardiac procedures where access to the left heart (left atrium or left ventricle) is required. For example, the apparatus can be used in a fluoroscopy-free left atrial arrhythmia ablation procedure. Here, the sheath 110 is inserted into a femoral vein and routed to the right atrium under electromagnetic guidance for positioning at the foramen ovale. Magnetic guidance can be achieved using a Carto® 3 system (Biosense Webster, Diamond Bar, California), as described above, or with other similar systems. In some examples, the site of the foramen ovale can be pre-identified using the catheter that creates the original geometry of the right atrium. As described above, for transseptal access, the transseptal needle 130 is extended out the distal end of dilator 120. Here, it can participate in electrogram recording, monitoring of the sheath location in three dimensional space, and transseptal radiofrequency ablation of the interatrial septum to allow advancement of the dilator 120 and sheath 110 into the left atrium. The other electrodes positioned at or near the distal ends of the dilator 120 and sheath 110 further facilitate mapping of the sheath 110 and dilator 120 within the cardiac chambers. During the course of the procedure, the other electrodes also enable electrogram monitoring (including monitoring of the left atrial tissue or pulmonary veins). The ability to record intracardiac electrograms from the transseptal apparatus 100 advantageously decreases the need to employ additional mapping catheters.

A number of embodiments of the invention have been described. Nevertheless, it will be understood that various modifications may be made without departing from the spirit and scope of the invention. Accordingly, other embodiments are within the scope of the following claims.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. An apparatus comprising:
   a sheath comprising a proximal end, a distal end, an outer surface having a diameter sized for introduction into a blood vessel of a subject, and a lumen extending between the proximal and distal ends of the sheath;
   a sheath electrode coupled to the sheath at or near the distal end of the sheath;
   a tapered dilator positioned within the sheath lumen and extending distally past the distal end of the sheath, the dilator comprising a proximal end, a distal end, and a lumen extending between the proximal and distal ends of the dilator;
   a dilator electrode coupled to the dilator at or near the distal end of the dilator;
   a transseptal needle retractably positioned within the dilator lumen, the transseptal needle comprising a proximal end and a distal end, the distal end of the transseptal needle comprising a transseptal needle electrode and a magnetic field sensor configured to detect the strength of a magnetic field; and
   a lead connected to the sheath electrode;
   wherein the transseptal needle electrode, the dilator electrode, and the sheath electrode are telescopically movable with respect to each other;
   wherein the magnetic field sensor is telescopically movable with respect to the dilator and the sheath; and
   wherein the sheath electrode forms a bipolar electrode pair with the dilator electrode to record electrograms.

2. The apparatus of claim 1, further comprising a transseptal needle lead in electrical conductance with the transseptal needle electrode.

3. The apparatus of claim 1, wherein the transseptal needle is configured to induce focal ablation of an atrial septum.

4. The apparatus of claim 3, wherein the transseptal needle is a radiofrequency trans septal needle.

5. The apparatus of claim 1, wherein the dilator electrode comprises a conductive material.

6. The apparatus of claim 1, wherein the dilator electrode is circumferentially disposed around at least a portion of the dilator.

7. The apparatus of claim 1, further comprising a dilator lead connected to the dilator electrode.

8. The apparatus of claim 1, further comprising a fourth electrode positioned proximal to the transseptal needle electrode.

9. The apparatus of claim 8, further comprising a fifth electrode positioned proximal to the transseptal needle electrode.

10. The apparatus of claim 1, wherein the diameter of the outer surface of the sheath is from 6 to 11 French.

11. The apparatus of claim 1, wherein the dilator electrode is positioned proximally from 1 to 10 mm from the distal end of the dilator.

12. The apparatus of claim 1, wherein the dilator electrode is suitable for electromagnetic positioning and electrogram recording.

13. The apparatus of claim 1, wherein the transseptal needle electrode is suitable for electromagnetic positioning, electrogram recording, and radiofrequency puncturing.

14. The apparatus of claim 1, wherein a distance between the distal end of the sheath and the distal end of the dilator is from 1 to 3 millimeters.

15. The apparatus of claim 1, wherein the transseptal needle comprises an electrically insulating material.

16. The apparatus of claim 1, wherein the transseptal needle comprises an inner lumen.

17. The apparatus of claim 1, wherein one or more of the transseptal needle electrode, the dilator electrode, and the sheath electrode are configured for electromagnetic positioning.

18. The apparatus of claim 1, wherein one or more of the transseptal needle electrode, the dilator electrode, and the sheath electrode are configured for electrogram recording.

* * * * *